(12) United States Patent
Li

(10) Patent No.: US 10,976,018 B2
(45) Date of Patent: *Apr. 13, 2021

(54) IMITATION CANDLE DEVICES WITH MOVING LIGHTS

(71) Applicant: L&L Candle Company, LLC, Brea, CA (US)

(72) Inventor: Xiaofeng Li, Shenzhen (CN)

(73) Assignee: L&L Candle Company, LLC, Brea, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/781,865

(22) Filed: Feb. 4, 2020

(65) Prior Publication Data

US 2020/0173620 A1 Jun. 4, 2020

Related U.S. Application Data

(63) Continuation of application No. 16/103,424, filed on Aug. 14, 2018, now Pat. No. 10,557,604, which is a
(Continued)

(30) Foreign Application Priority Data

Jun. 12, 2017 (CN) .......................... 201720681557.5

(51) Int. Cl.
*F21S 10/04* (2006.01)
*F21S 19/00* (2006.01)
(Continued)

(52) U.S. Cl.
CPC ............... *F21S 10/04* (2013.01); *F21S 6/001* (2013.01); *F21S 19/00* (2013.01); *F21V 14/02* (2013.01);
(Continued)

(58) Field of Classification Search
CPC .......... F21S 10/04; F21S 10/046; F21S 19/00; F21S 6/001; F21V 14/02; F21V 14/025;
(Continued)

(56) References Cited

U.S. PATENT DOCUMENTS 6,491,516 B1 12/2002 Tal et al.
7,837,355 B2 11/2010 Schnuckle
(Continued)

FOREIGN PATENT DOCUMENTS

CA 2779978 1/2016
CA 2886665 8/2016
(Continued)

OTHER PUBLICATIONS

German Office Action issued for German Patent Application No. 102016008225.9, dated Dec. 19, 2016.
(Continued)

*Primary Examiner* — Alan B Cariaso
(74) *Attorney, Agent, or Firm* — Perkins Coie LLP

(57) ABSTRACT

Imitation candle devices and systems with features enable simulation of a realistic candle flame using moving lights are disclosed. In one aspect, an imitation candle device is provided that includes a flame sheet shaped to resemble a flame, a support member positioned in proximity to the flame sheet, and a light casing including a hole. An end of the support member extends into the hole and a tip of the end of the support member is in contact with an inner wall of the hole to allow movement of the light casing on the support member. The imitation candle device also includes a light emitter enclosed at least partially in the light casing and movable with movement of the light casing. The light emitter is oriented at an inclined angle with respect to the flame sheet to emit light onto the flame sheet.

14 Claims, 9 Drawing Sheets

Related U.S. Application Data continuation of application No. 15/630,746, filed on Jun. 22, 2017, now Pat. No. 10,054,276.

(51) Int. Cl.

| | |
|---|---|
| *F21V 14/02* | (2006.01) |
| *F21S 6/00* | (2006.01) |
| *F21W 121/00* | (2006.01) |
| *H05B 39/09* | (2006.01) |
| *H05B 47/10* | (2020.01) |

(52) U.S. Cl.
CPC ............ *H05B 39/09* (2013.01); *H05B 47/10* (2020.01); *A61L 2209/12* (2013.01); *F21W 2121/00* (2013.01)

(58) Field of Classification Search
CPC ......... F21W 2121/00; F21W 2121/002; H05B 39/09; A61L 2209/12; Y10S 362/81
See application file for complete search history.

(56) References Cited

U.S. PATENT DOCUMENTS

| | | |
|---|---|---|
| 8,070,319 B2 | 12/2011 | Schnuckle et al. |
| 8,132,936 B2 | 3/2012 | Patton et al. |
| 8,210,708 B2 | 7/2012 | Hau et al. |
| 8,342,712 B2 | 1/2013 | Patton et al. |
| 8,454,190 B2 | 6/2013 | Hau et al. |
| 8,534,869 B2 | 9/2013 | Patton et al. |
| 8,550,660 B2 | 10/2013 | Patton et al. |
| 8,646,946 B2 | 2/2014 | Schnuckle et al. |
| 8,696,166 B2 | 4/2014 | Patton et al. |
| 8,721,118 B2 | 5/2014 | Patton et al. |
| 8,727,569 B2 | 5/2014 | Schnuckle et al. |
| 8,733,986 B2 | 5/2014 | Hau et al. |
| D729,424 S | 5/2015 | Li |
| 9,033,553 B2 | 5/2015 | Li |
| D739,573 S | 9/2015 | Li |
| D744,128 S | 11/2015 | Li |
| D748,298 S | 1/2016 | Li |
| D757,306 S | 5/2016 | Li |
| D757,335 S | 5/2016 | Li |
| D757,336 S | 5/2016 | Li |
| D757,337 S | 5/2016 | Li |
| 9,335,014 B2 | 5/2016 | Patton et al. |
| D759,858 S | 6/2016 | Li |
| D759,879 S | 6/2016 | Li |
| D759,880 S | 6/2016 | Li |
| D760,405 S | 6/2016 | Li |
| D760,422 S | 6/2016 | Li |
| D760,423 S | 6/2016 | Li |
| D760,424 S | 6/2016 | Li |
| 9,360,181 B2 | 6/2016 | Li |
| 9,366,402 B2 | 6/2016 | Li |
| 9,371,972 B2 | 6/2016 | Li |
| 9,371,973 B2 | 6/2016 | Li |
| D763,479 S | 8/2016 | Li |
| D767,799 S | 9/2016 | Li |
| D767,810 S | 9/2016 | Li |
| 9,447,938 B2 | 9/2016 | Li |
| D774,474 S | 12/2016 | Li |
| D774,478 S | 12/2016 | Li |
| 9,512,971 B2 | 12/2016 | Li |
| 9,518,710 B2 | 12/2016 | Li |
| 9,523,471 B2 | 12/2016 | Li |
| 9,551,470 B2 | 1/2017 | Li |
| 9,585,980 B1 | 3/2017 | Li |
| 9,605,824 B1 | 3/2017 | Li |
| 9,625,112 B2 | 4/2017 | Li |
| 9,664,344 B2 | 5/2017 | Hau et al. |
| D789,570 S | 6/2017 | Li |
| D790,749 S | 6/2017 | Li |
| 9,689,538 B2 | 6/2017 | Hau et al. |
| D791,391 S | 7/2017 | Li |
| D791,392 S | 7/2017 | Li |
| D792,634 S | 7/2017 | Li |
| 9,709,231 B2 | 7/2017 | Li |
| 10,054,276 B1 * | 8/2018 | Li ........................... F21V 14/02 |
| 10,557,604 B2 * | 2/2020 | Li ........................... F21V 14/02 |
| 2005/0007779 A1 | 1/2005 | Nozawa et al. |
| 2006/0192503 A1 | 8/2006 | Trombetta et al. |
| 2008/0151571 A1 | 6/2008 | Chen |
| 2010/0207538 A1 | 8/2010 | Chen |
| 2011/0000666 A1 | 1/2011 | Couto |
| 2011/0195787 A1 | 8/2011 | Wells |
| 2012/0093491 A1 | 4/2012 | Browder et al. |
| 2014/0035483 A1 | 2/2014 | Becker et al. |
| 2014/0140042 A1 | 5/2014 | Schreiber |
| 2014/0218929 A1 | 8/2014 | Schnuckle et al. |
| 2014/0268652 A1 | 9/2014 | Li |
| 2014/0286024 A1 | 9/2014 | Li |
| 2015/0070874 A1 | 3/2015 | Beesley et al. |
| 2015/0285453 A1 | 10/2015 | Schnuckle et al. |
| 2015/0292698 A1 | 10/2015 | Schnuckle et al. |
| 2015/0362141 A1 | 12/2015 | Chen |
| 2016/0029461 A1 | 1/2016 | Noh et al. |
| 2016/0057829 A1 | 2/2016 | Li |
| 2017/0191633 A1 * | 7/2017 | Patton .................. G02B 6/0008 |
| 2017/0211767 A1 * | 7/2017 | Baeza .................... F21V 14/02 |

FOREIGN PATENT DOCUMENTS

| | | |
|---|---|---|
| CN | 204268356 | 4/2015 |
| DE | 212011100014 | 4/2012 |
| DE | 202015102274 | 5/2015 |
| EP | 1639291 | 5/2009 |
| EP | 2587127 A | 5/2013 |
| GB | 2267746 | 12/1993 |
| GB | 2443926 | 5/2008 |
| GB | 2527626 | 12/2015 |
| WO | WO2012099718 | 7/2012 |
| WO | WO2013020439 | 2/2013 |
| WO | WO2014139483 | 9/2014 |
| WO | WO2016000517 | 1/2016 |

OTHER PUBLICATIONS

Canadian Examination Report issued for Canadian Patent Application No. 2930099, dated Jan. 5, 2017.
Canadian Examination Report issued for Canadian Patent Application No. 2930099, dated Aug. 15, 2016.
Combined Search and Examination Report in British Patent Application No. 1613387.8, dated Sep. 9, 2016.
Canadian Examination Report issued for Canadian Patent Application No. 2936225, dated Sep. 29, 2016.
German Office Action issued for German Patent Application No. 102016008825.7, dated Mar. 20, 2017.
Combined Search and Examination Report in British Patent Application No. 1613393.6, dated Sep. 9, 2016.

* cited by examiner

IMITATION CANDLE DEVICES WITH MOVING LIGHTS

CROSS-REFERENCE TO RELATED APPLICATIONS

This application is a continuation of U.S. patent application Ser. No. 16/103,424, filed Aug. 14, 2018, which is continuation of U.S. patent application Ser. No. 15/630,746, filed Jun. 22, 2017, which further claims the benefits and priorities of Chinese patent application no. CN 201720681557.5 filed on Jun. 12, 2017.

TECHNICAL FIELD

The subject matter of this patent document relates to a candle devices that use an imitation flame, and particularly, to features that enhance the use and realistic appearance of imitation candle devices.

BACKGROUND

Traditional true flame candles, when lit, provide a pleasant ambience in many homes, hotels, churches, businesses, etc. Traditional candles, however, provide a variety of hazards including risk of fire, damage to surfaces caused by hot wax, and the possible emission of soot. Flameless candles have become increasingly popular alternatives to traditional candles. With no open flame or hot melted wax, flameless candles provide a longer-lasting, safe, and clean alternative. Such imitation candle devices often include light sources, such as LEDs, and include electronic circuits that control the operation the imitation candle device.

SUMMARY OF PARTICULAR EMBODIMENTS

The disclosed embodiments relate to devices and methods for imitating the appearance of real candles using electronic candle devices.

In one exemplary aspect, an imitation candle device is disclosed. The imitation candle device includes a flame sheet shaped to resemble a flame; a support member positioned in proximity to the flame sheet; a light casing including a hole, wherein an end of the support member extends into the hole and a tip of the end of the support member is in contact with an inner wall of the hole to allow movement of the light casing on the support member; a light emitter enclosed at least partially in the light casing and movable with movement of the light casing, the light emitter oriented at an inclined angle with respect to the flame sheet to emit light onto the flame sheet; and a drive engine coupled to the light casing to cause the light casing to sway on the support member and to cause the light emitted from the light emitter to impinge upon the flame sheet resembling a flickering flame.

In another exemplary aspect, an imitation candle device is disclosed. The imitation candle device includes an outer shell having a shape to resemble a real candle; a flame sheet shaped to resemble a flame; a core positioned inside the outer shell, the core including an opening to allow the flame sheet to be exposed above the core; a support member enclosed by the core; a light casing including a hole, wherein an end of the support member extends into the hole and a tip of the end of the support member is in contact with an inner wall of the hole to allow a movement of the light casing on the support member within the inner shell; and a light emitter enclosed at least partially by the light casing and movable with movement of the light casing, the light emitter oriented at an inclined angle with respect to the flame sheet to emit light onto the flame sheet, wherein the core includes a limiting structure positioned in proximity of the light casing to limit the movement of the light casing.

The above and other aspects and their implementations are described in greater detail in the drawings, the description and the claims.

DETAILED DESCRIPTION

In this patent document, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

An imitation candle device can simulate a real candle with a flame that resembles a real-life flame having flickering effects using optical, mechanical and electrical components. The disclosed embodiments provide features and functionalities for imitation candle devices that include moving lights to illuminate a flame sheet to resemble the appearance of real flames.

Figure 1A:
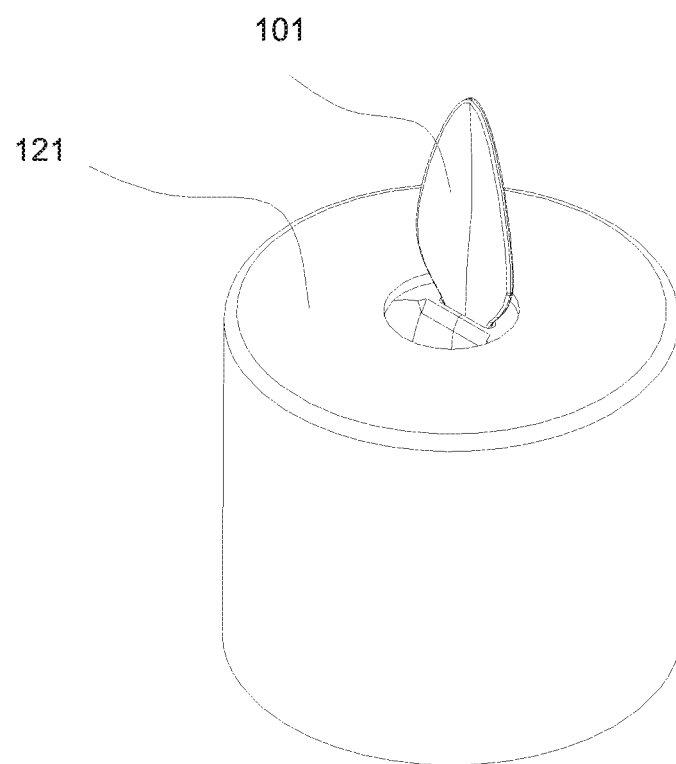
FIG. 1A illustrate an exemplary imitation candle device that includes a flame sheet and a shell that covers the internal components of the imitation candle device.

FIG. 1A illustrates an exemplary imitation candle device 100 that includes a flame element 101 and a shell 121 that covers the internal components of the imitation candle device. For example, the shell 121 covers a base 107 (see, e.g., FIG. 1B), a light source 102 and a central control circuit (not shown). The shell can have a wax-like surface to mimic the appearance of a real candle.

Figure 1B:
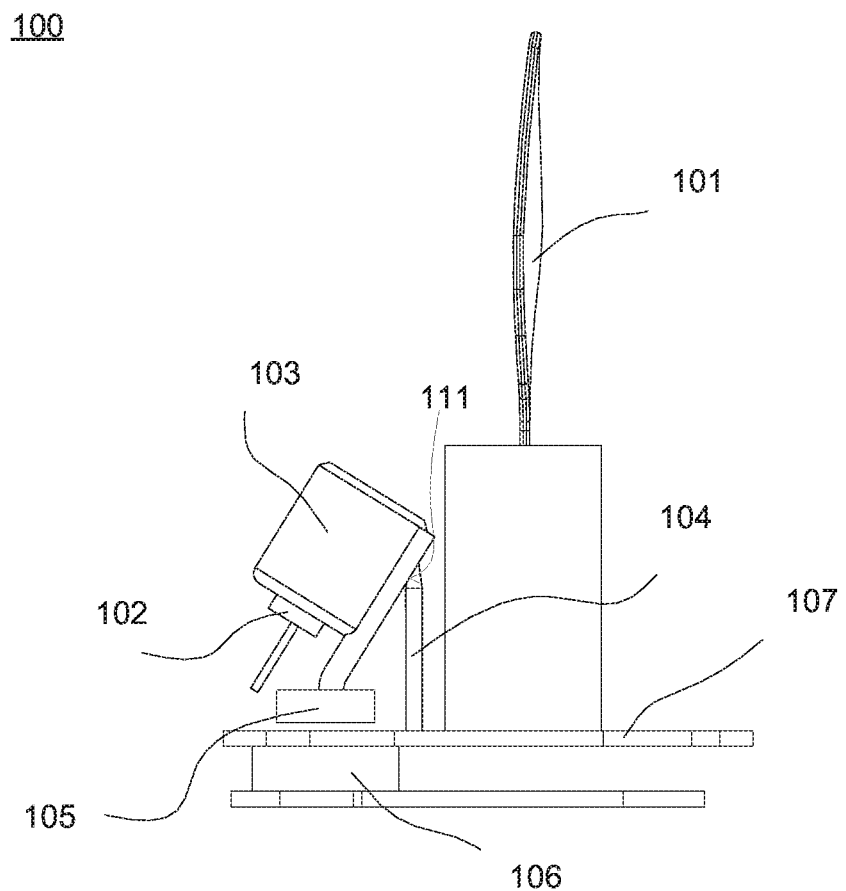
FIG. 1B shows a side view of exemplary internal components of an imitation candle device.
Figure 1C:
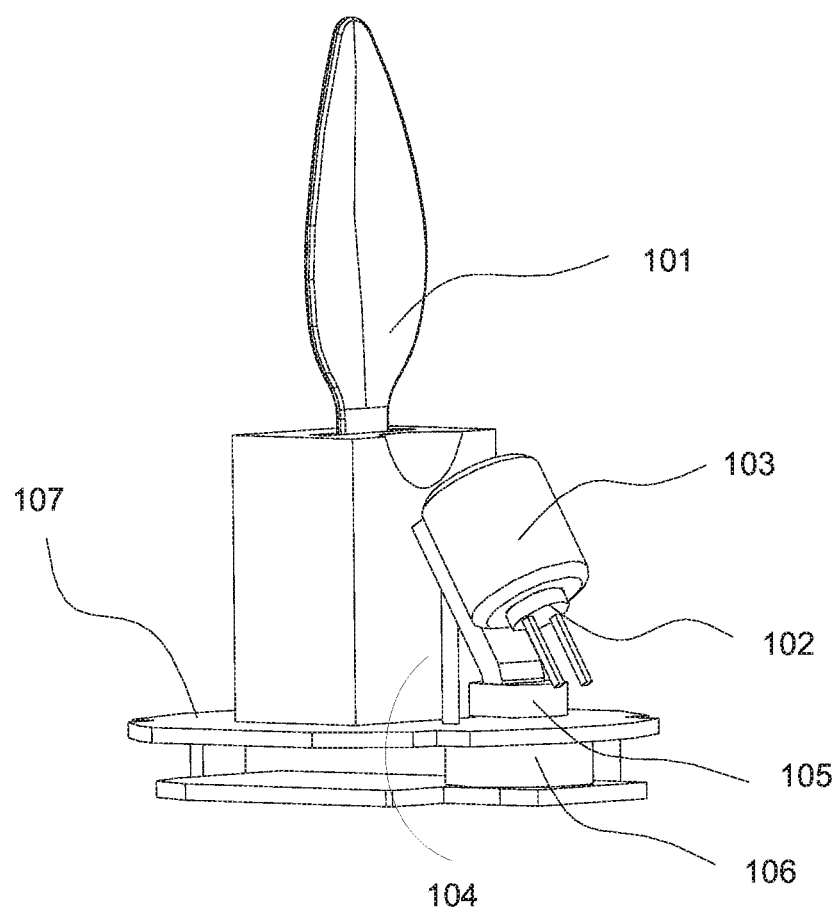
FIG. 1C shows an isometric view of exemplary internal components of an imitation candle device.

FIG. 1B shows a side view of exemplary internal components of an imitation candle device having one or more moving lights. FIG. 1C shows an isometric view of exemplary internal components of an imitation candle device having one or more moving lights. The imitation candle device 100 comprises a flame sheet 101, a light emitter 102, a light casing 103, and a support member 104. In some embodiments, the flame sheet 101 is shaped to mimic the appearance of real flames. The light emitter 102 may include multiple light sources. For example, the light emitter 102 can be an LED light source or can include multiple LED emitters. The light emitter 102 is oriented at an inclined angle with respect to the flame sheet 101 to emit light onto the flame sheet 101.

As shown in FIGS. 1B-1C, the light emitter 102 is enclosed at least partially in the light casing 103. One side of the light casing 103 is coupled to an end 111 of a support member 104 positioned close to the flame sheet 101. In some embodiment, the end 111 extends vertically from the body of the support member 104 into the light casing 103. The end 111 of the support member 104 is positioned against an inner wall of the light casing 103, thereby providing support for the light casing 103 so that the light emitter 103 enclosed in the light casing 103 can sway back and forth with the light casing 103 and emit moving light onto the flame sheet 101. The tip of the end 111 may also include additional parts that extend horizontally, or outwardly, from the body of the support member 104 to ensure that the light casing 103 does not easily fall off the support member 104 due to its motion.

The imitation candle device 100 further includes a base 107 to mount the support member 104. A coil 106 can be positioned beneath the base 107 and be controlled by an electronic control circuit of the imitation device to produce a varying magnetic field. One end of the light casing 103 is coupled to a magnetic member 105 that is suspended over the base 107 and the corresponding coil 106. The magnetic field produced by the coil 106 exerts a force on the magnetic member 105 to cause the light casing 103 to sway or move. As a result, the light emitted by the light source onto the flame sheet 101 appears as a flickering light similar to a real flame.

In some embodiments, a motor is coupled to the light casing instead of the magnetic member 105. The motor can by controlled by the central control circuit to move the light casing 103 so that the light emitted on the flame sheet 101 appears as a flickering light similar to a real flame.

Figure 2:
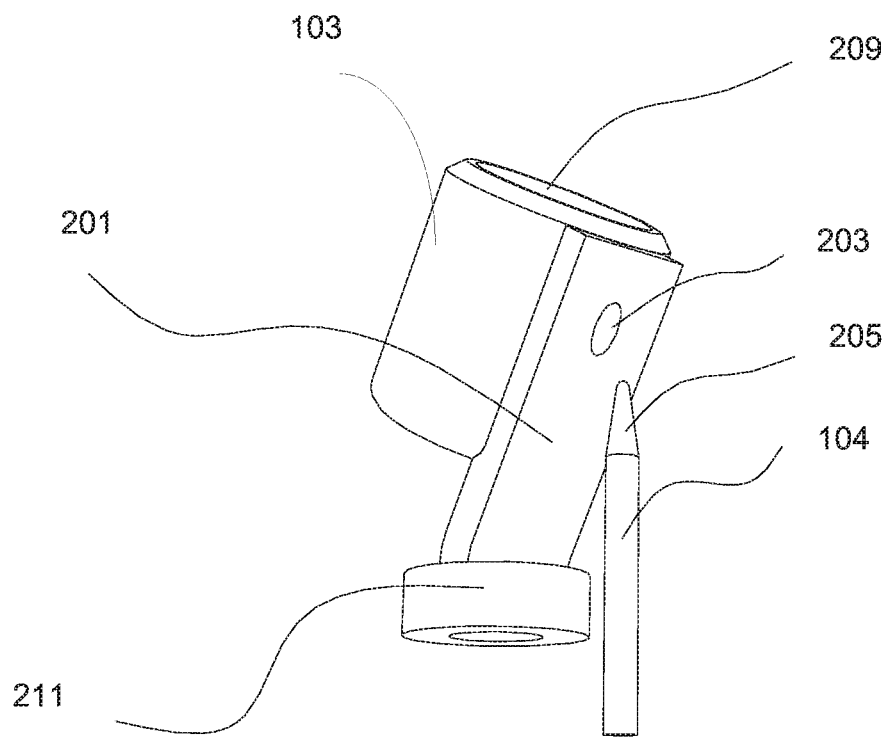
FIG. 2 shows an exemplary support member and a corresponding light casing.

FIG. 2 shows an exemplary support member 104 and the corresponding light casing 103. In this embodiment, a light emitter 209 is fully enclosed by a light casing 103. The light casing 103 includes a coupling piece 201 to couple a magnetic component 211 to the bottom of the light casing. The light casing 103 also includes a support hole 203 located at one side of the coupling piece 201. A top end 205 of a support member 207 extends into the support hole 203 and is positioned against an inner wall of the support hole 203 so that the contact between the support hole 203 and the top end 205 becomes a pivot point for the light casing 203 to form a swaying motion under the magnetic force exerted on the magnetic component 211. In some embodiments, the top end 205 of the support member 207 has a tapered shape to facilitate placement of the light casing 201 on the support member 207. In some embodiments, the tip of the top end 205 has a spherical shape to allow smooth motion of the light casing 201 against the support member 207.

In some implementations, such as the embodiment shown in FIG. 2, the support hole itself limits the movement of the light casing. However, in some embodiments, the size of the flame sheet is relatively small. In such embodiments, to ensure that the light emitted from the light emitter falls on the flame sheet, the movement of the light emitter needs to be constrained within a small range. The support hole thus needs to be very small, which increases the complexity of manufacturing and assembly. Therefore, it is may be preferable to restrict the swaying movement of the light casing (and/or the light source) while maintaining a reasonably large support hole. To this end, in some embodiments, the support hole includes an additional limiting structure to constrain the movement of the light casing. The limiting structure forms a defined space that limits the movement of the end of the support member within the support hole, thereby preventing the emitted light from moving off the flame sheet. The use of the limiting structure also prevents the support hole from colliding into the support member, which can produce undesirable thumping sounds and cause sudden movements of the light emitter that appear unnatural.

Figure 3A:
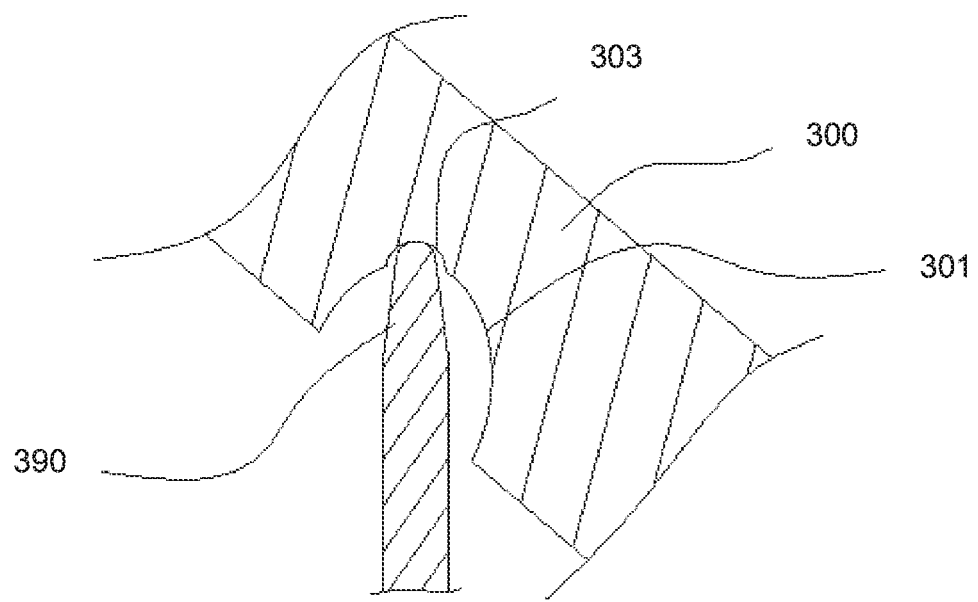
FIG. 3A depicts an exemplary support hole of the light casing that includes a recess.

For example, FIG. 3A shows an exemplary limiting structure within a support hole. The support hole 301 of the light casing 300 includes a recess 303 from the support hole 301. The recess forms a space that accommodates an end of the support member 390. The recess 303 also limits the movement between the light casing 300 and the support member 390 so that the angle of the swaying motion is not too large. In some embodiments, the recess 303 is at least partially shaped as a spherical recess. The end of the support member 390 can have a corresponding spherical shape so that the movement of the light casing 300 on the support member 390 is smooth.

Figure 3B:
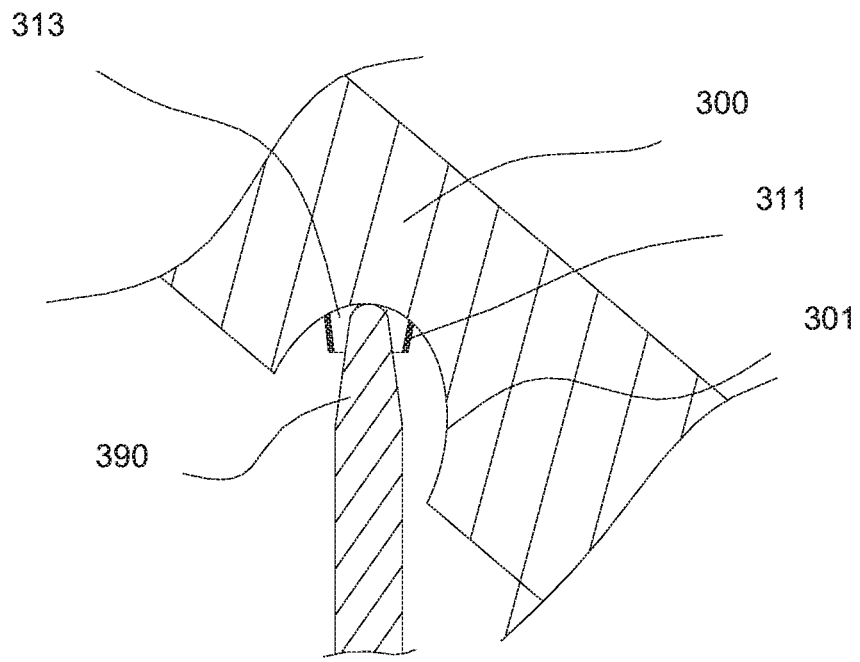
FIG. 3B depicts an exemplary support hole of the light casing that includes a protruding wall.

FIG. 3B shows another exemplary limiting structure within a support hole. In this embodiment, the limiting structure includes a protruding wall 311 that protrudes from an inner surface of the support hole 301. In some embodiments, the protruding wall 311 has a tubular shape and forms a space 313 to accommodate an end of the support member 390. In some embodiments, a vertical section of the protruding wall 311 has a trapezoid shape. In some implementations, the protruding wall 311 has a uniform cross section and forms a cylindrical shape. The protruding wall 311 can be an integral part protruding from the surface of the support hole 301. In some embodiments, multiple separate raised subparts can extend from the inner surface of the support hole 301 to form the protruding wall 311. The protruding wall 311 limits the movement between the light casing 300 and the support member 390 so that the angle of the swaying motion is not too large.

Figure 3C:
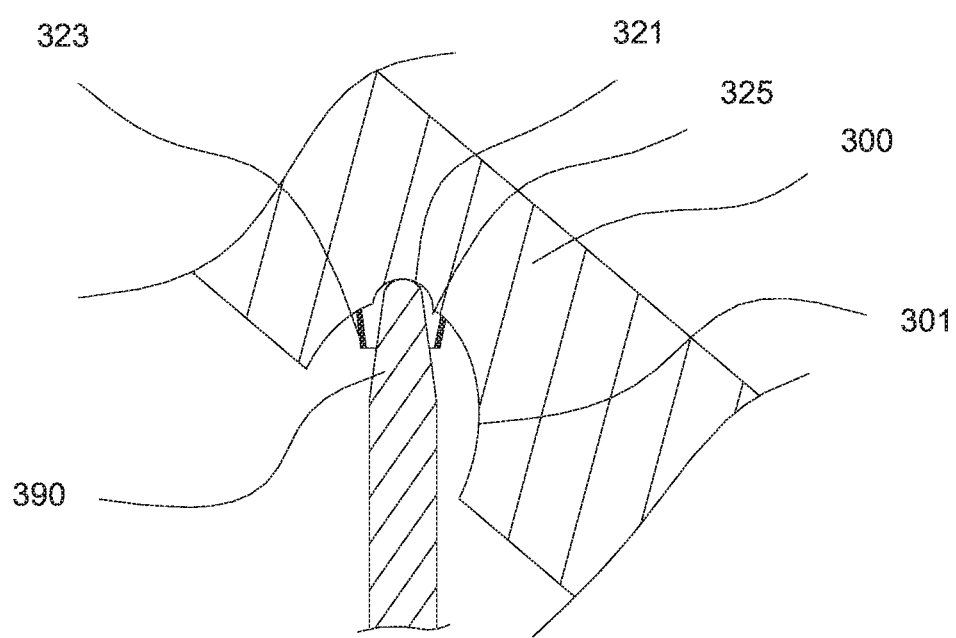
FIG. 3C depicts an exemplary support hole of the light casing that includes a recess and a protruding wall.

FIG. 3C shows yet another exemplary limiting structure within a support hole. In this embodiment, the limiting structure includes both a recess 321 and a protruding wall 323 to form a space 325 in order to accommodate an end of the support member 390. The recess 321, as well as the raised part 323, limit the movement between the light casing 300 and the support member 390 so that the angle of the swaying motion is not too large.

The specific configurations to the support member and light casing depicted in FIGS. 3A-C and described above are made to illustrate examples on a pivoting mechanism can be formed between these two parts. It is however understood that other configurations can be assigned to those components. For example, the support member can have various shapes, such as a tubular member (as shown in FIGS. 1B-3B) or a rectangular pillar. In some embodiments, instead of having a support hole, the light casing can include a protruded part that accommodates an end of the support member. The protruded part may have a spherical shape to allow movement of the light casing in various directions and angles. For example, the protruded part and the end of the support member can form a ball joint. The protruded part may include additional limiting structures within the ball joint to limit the angle and direction of movement.

Figure 4:
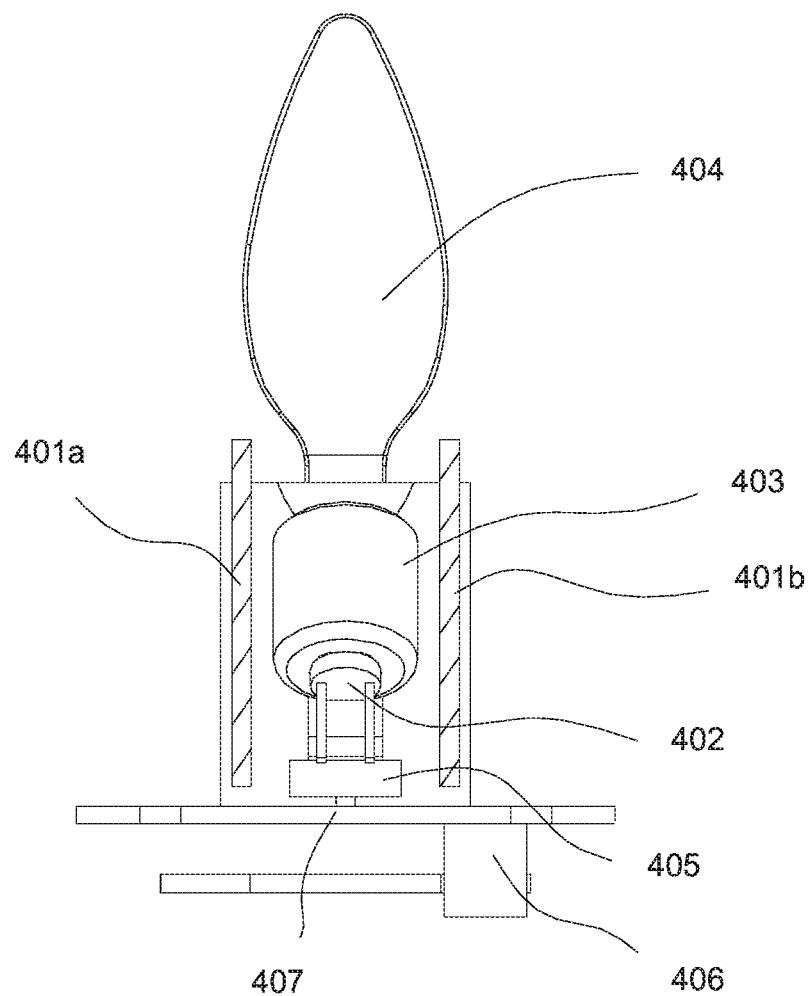
FIG. 4 shows an exemplary limiting structure positioned outside of the light casing.

In some embodiments, additional components can be used to further limit the movement of the light casing. FIG. 4 shows an exemplary limiting structure positioned outside of the light casing. In this example, the light emitter 402 is partially enclosed by the light casing 403. The limiting structure includes two baffles 401a and 401b positioned in parallel at each side of the light casing 403. The baffles 401a and 401b act as a stopper to stop the light casing 403 from extra movement in the X direction. In some embodiments, additional baffles can be posited at other sides of the light casing 403 to limit its movement in the Y direction. In this particular example, the central control circuit controls the coil 406 to generate a varying magnetic field, exerting a force on the magnetic member 405 coupled to the bottom section of the light casing 403. The magnetic member 405, under the influence of the magnetic force, causes the light casing 403 to sway back and forth in both X and Y directions. The movement of the light casing 403 may be limited by a support hole of the light casing, such as described above. The movement can be further limited by baffles 401a and 401b in the X direction. The light emitted onto the flame sheet 404 by the light emitter 402, therefore, moves back and forth accordingly, forming a flickering appearance that resembles real flames.

Figure 5:
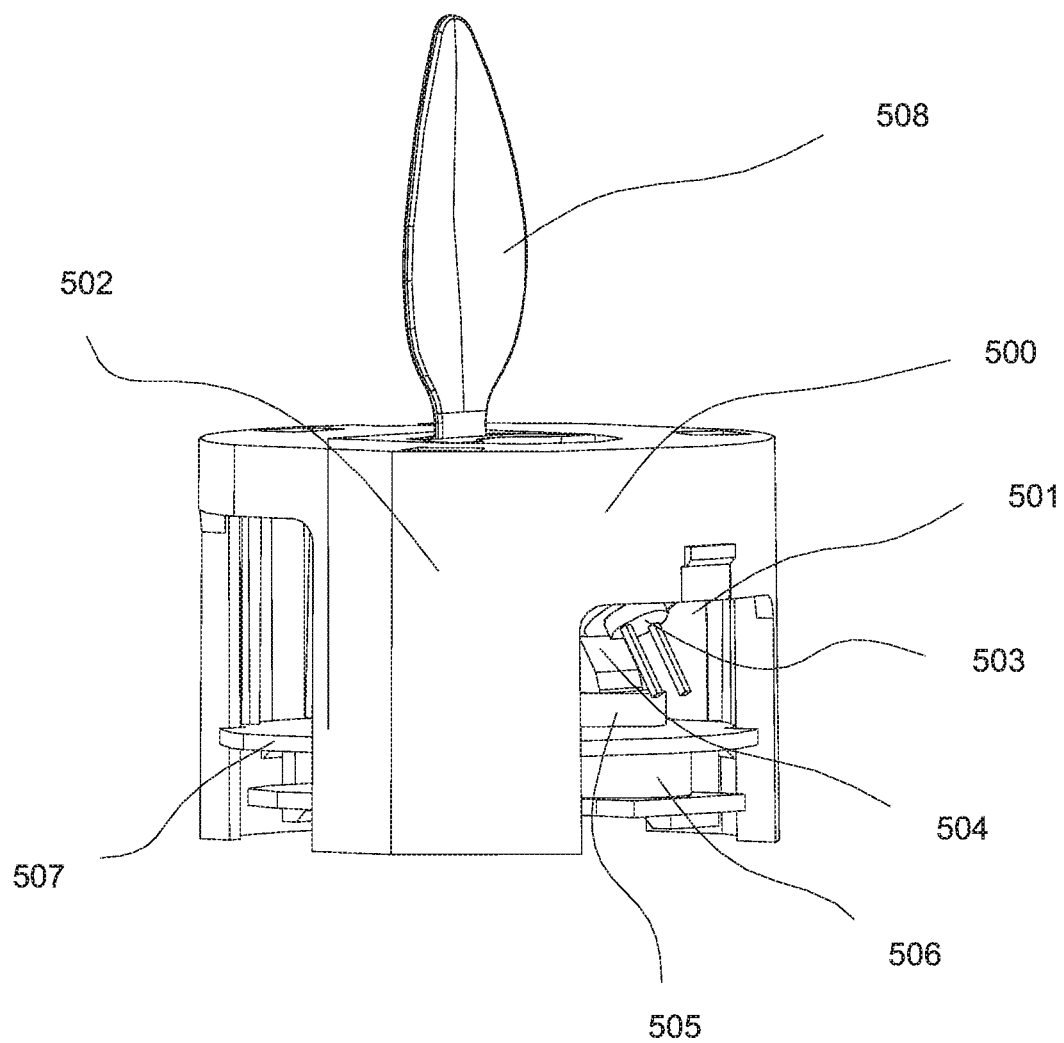
FIG. 5 shows an exemplary core of an imitation candle device that includes a structure to constrain the movement of the light casing.

The shape and the location of the baffles can also be adapted to the shape of the imitation candle device. FIG. 5 shows an exemplary core 500 of an imitation candle device that acts as an external limiting structure to limit the movement of the light casing. For example, an internal side wall 501 of the core acts as a first baffle to the light casing 504. Similarly, another internal side wall 502 of the core (hidden within the core) acts as a second baffle to the light casing 504. Based on the movement of the light casing 504, the internal side walls 501 and 502 may have curved shapes, or form a tapered space for the light casing 504, such that they can effectively stop extra movement of the light casing 504 without introducing unnecessary collisions and associated noise. The core can optionally include more internal structures to further limit the movement of the light casing 504 in other directions. The core 500 can be manufactured using one mold, thereby eliminating the need of manufacturing and assembling separate parts for the imitation candle device. In this example, the central control circuit controls the coil 506 to generate a varying magnetic field, exerting a force on the magnetic member 505 that is coupled to the bottom section of the light casing 504. The magnetic member 505, under the influence of the magnetic force, causes the light casing 504 to sway back and forth. The movement of the light casing 504 may be limited by the support hole as described above, and can be further limited by the internal side walls of the core (e.g., 501 and 502). The light emitted onto the flame sheet 508 by the light emitter 503, therefore, moves back and forth accordingly, forming a flickering appearance that resembles real flames.

It is thus evident that, in one aspect of the disclosed technology, an imitation candle device is provided that includes a flame sheet shaped to resemble a flame, a support member positioned in proximity to the flame sheet, and a light casing including a hole. An end of the support member extends into the hole and a tip of the end of the support member is in contact with an inner wall of the hole to allow movement of the light casing on the support member. The imitation candle device also includes a light emitter enclosed at least partially in the light casing and movable with movement of the light casing. The light emitter is oriented at an inclined angle with respect to the flame sheet to emit light onto the flame sheet. The imitation candle device further includes a drive engine coupled to the light casing to cause the light casing to sway on the support member and to cause the light emitted from the light emitter to impinge upon the flame sheet resembling a flickering flame. In some embodiments, the end of the support member has a tapered shape. The tip of the end of the support member can have a spherical shape.

In some embodiments, the hole includes a recess and the end of the support member extends into the recess and the tip of the end of the support member is in contact with an inner wall of the recess. In some embodiments, at least a part of the recess has a spherical shape.

In some embodiments, the hole can include a tubular section protruding from the inner wall of the hole and the end of the support member extends into the tubular section such that the sway of the light casing is partially restricted by tubular section. In some implementations, the tubular section has a cylindrical shape.

In some embodiments, the hole includes a recess and a tubular section surrounding the recess such that the end of the support member extends into the tubular section and the tip of the end of the support member being in contact with an inner wall of the recess.

In some embodiments, the imitation candle device further includes a limiting structure positioned outside of the light casing to partially restrict the sway of the light casing. The limiting structure includes a plurality of baffles, each of the baffles positioned at one side of the light casing to partially restrict the sway of the light.

In some embodiments, the imitation candle device further includes a magnetic member coupled to a lower portion of the light casing, The drive engine includes a coil in proximity of the magnetic member such that upon interaction of the magnetic member with a magnetic field of the coil, the light casing sways on the support member. In some implementations, the drive engine includes a motor coupled to the light casing. The motor is controlled by an electronic control circuit to cause the movement of the light casing.

In another aspect of the disclosed technology, an imitation candle device is provided that includes an outer shell having a shape to resemble a real candle, a flame sheet shaped to resemble a flame, a core positioned inside the outer shell including an opening to allow the flame sheet to be exposed above the core, a support member enclosed by the core, and a light casing including a hole. An end of the support member extends into the hole and a tip of the end of the support member is in contact with an inner wall of the hole to allow a movement of the light casing on the support member within the inner shell. The imitation candle device also includes a light emitter enclosed at least partially by the light casing and movable with movement of the light casing, the light emitter oriented at an inclined angle with respect to the flame sheet to emit light onto the flame sheet. The core includes a limiting structure positioned in proximity of the light casing to limit the movement of the light casing. In some embodiments, the end of the support member has a tapered shape. The tip of the end of the support member can have a spherical shape.

In some embodiments, the hole further includes a recess so that the end of the support member extends into the recess and the tip of the end of the support member is in contact with an inner wall of the recess. The recess can have a spherical shape.

In some embodiments, the hole includes a tubular section protruding from the inner wall of the support whole such that the end of the support member extends into the tubular section. The tubular section can have a cylindrical shape.

In some embodiments, the hole includes a recess and a tubular section surrounding the recess such that the end of the support member extends into the tubular section and the tip of the end of the support member being in contact with an inner wall of the recess.

In some embodiments, the imitation candle device further includes a limiting structure positioned outside of the light casing to partially restrict the sway of the light casing. The limiting structure can include a plurality of baffles, each of the baffles positioned at one side of the light casing.

In some embodiments, the imitation candle device also includes a magnetic component coupled to a lower portion of the light casing, an electronic control circuit, and a coil positioned in proximity of the magnetic member. The coil can be configured to receive an electrical signal from the electronic control circuit that energizes the coil to produce a changing magnetic field interacting with the magnetic component, thereby causing the movement of the light casing.

In some embodiments, the imitation candle device includes a motor coupled to the light casing and an electronic control circuit. The electronic control circuit can be configured to supply an electrical signal to the motor to cause the movement of the light casing.

In one aspect of the disclosed embodiments, the imitation candle device includes a cylindrical shell having a hollow interior and an opening on top of the cylindrical shell. The imitation candle device also includes a flame sheet shaped to resemble a flame and protruding vertically upward through the opening of the shell, as well as a light projection subsystem within the shell to project light onto a surface area of the flame sheet through the opening of the shell. The light projection subsystem includes a movable component operable to cause a change in a direction of the light emanating from the light projection subsystem onto the flame sheet. The imitation candle device further includes a magnetic member coupled to the movable component of the light projection subsystem, a coil, and an electronic circuit coupled to the coil and configured to energize the coil to produce a varying magnetic field that exerts a force on the magnetic member, thereby causing the magnetic member and the movable component of the light projection subsystem to move in response to the varying magnetic field.

In one exemplary embodiment, the imitation candle device further includes a support member upon which the movable component of the light projection subsystem sways back and forth in response to the varying magnetic field. In another exemplary embodiment, the imitation candle device further includes an elongated coupling piece that couples the magnetic member to the movable component of the light projection subsystem, where the magnetic member is attached to a bottom end of the elongated coupling piece. In one exemplary embodiment, the magnetic member has a circular cross section.

In another exemplary embodiment, the illumination assembly includes a casing and a light source that is at least partially positioned within the casing, where the casing is movable is response to the varying magnetic field. In one exemplary embodiment, the light source includes multiple light emitting devices (LEDs), while in another exemplary embodiment, the light source is oriented at an inclined angle with respect to the flame sheet. In yet another exemplary embodiment, the imitation candle device further includes a support member coupled to the casing of the light projection subsystem which allows the casing to sway back and forth when supported by the support member in response to the varying magnetic field. In still another exemplary embodiment, the casing includes a support hole and the support member comprises a vertical post that is received by the support hole. In another exemplary embodiment, the movable component of the light projection subsystem has a circular cross sectional area.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. An imitation candle device, comprising:
    a flame element having a flame-like shape;
    a light casing including a light emitter that is configured to emit light onto a surface of the flame element, the light casing having internal surfaces defining an opening, wherein the opening includes a recess, and wherein at least a part of the recess has a spherical shape;
    a support member, supporting the light casing to hold the light emitter at an angle to face the flame element and to emit light onto the flame element, wherein the support member has a tip extending from the support member, the tip of the support member fits in the opening of the light casing and extends into the recess, wherein the tip of the support member is in contact with an inner wall of the recess, and wherein the light casing is held on the support member in a way which allows movement of the light casing relative to the support member;
    a drive engine coupled to the light casing, and configured to cause the light casing to move on the support member and to move the light emitted from the light emitter on the flame element; and
    a movement limiting structure that limits an amount of the movement of the light casing relative to the support member in a range that prevents the light emitted by the light emitter from moving off the flame element.

2. The device of claim 1, wherein the movement limiting structure is in the opening.

3. The device of claim 1, wherein the movement limiting structure includes a plurality of baffles, wherein each of the baffles is positioned at a side of the light casing to partially restrict the sway of the light.

4. The device of claim 3, wherein the baffles are positioned to interact with the tip of the support member.

5. The device of claim 1, wherein the movement limiting structure is positioned outside of the light casing.

6. The device of claim 1, where the drive engine includes a magnetic member coupled to a lower portion of the light casing.

7. The device of claim 6, where the drive engine includes a coil in a proximity of the magnetic member such that upon interaction of the magnetic member with a magnetic field of the coil, the light casing sways relative to the support member.

8. The device of claim 6, wherein the magnetic member has a circular cross section.

9. The device of claim 1, where the drive engine includes a motor coupled to the light casing, and an electronic control circuit to cause the movement of the light casing.

10. A method of lighting an imitation candle device, comprising:
   attaching a flame element having a flame shape to a body of an imitation candle device;
   emitting light from a light emitter;
   supporting the light emitter to hold the light emitter at an angle to face the flame element and to emit light onto the flame element, and allowing the light emitter to move relative to the support member;
   energizing a drive engine to cause a light casing to move on the support member and thus to move a position of the light that is emitted from the light emitter on to the flame element; and
   limiting an amount of the movement of the light casing relative to the support member in a range that prevents the emitted light from moving off the flame element,
   wherein the limiting is carried out by a movement limiting structure which includes a plurality of baffles, and wherein each of the baffles in the plurality of baffles is positioned to interact with a tip of the support member.

11. The method as in claim 10, wherein said light casing has internal surfaces defining an opening, wherein the the tip of the support member extends from the support member, and the tip of the support member fits in the opening of the light casing, wherein the light casing is held on the support member, and wherein said light casing is configured to move relative to the support member.

12. The method of claim 10, wherein the movement limiting structure is positioned outside of the light casing.

13. A method of lighting an imitation candle device, comprising:
   attaching a flame element having a flame shape to a body of an imitation candle device;
   emitting light from a light emitter, wherein the light emitter is incorporated in a light casing, wherein the light casing has internal surfaces defining an opening, wherein the opening includes a recess, and wherein at least a part of the recess has a spherical shape;
   supporting the light emitter to hold the light emitter at an angle to face the flame element and to emit light onto the flame element, and allowing the light emitter to move relative to a support member, wherein the support member has a tip extending from the support member, the tip of the support member fits in the opening of the light casing and extends into the recess, wherein the tip of the support member is in contact with an inner wall of the recess, and wherein the light casing is held on the support member in a way which allows movement of the light casing relative to the support member;
   energizing a drive engine to cause the light casing to move on the support member and thus to move a position of the light that is emitted from the light emitter on the flame element; and
   limiting an amount of the movement of the light casing relative to the support member in a range that prevents the emitted light from moving off the flame element.

14. An imitation candle device, comprising:
   a flame element having a flame-like shape;
   a light casing including a light emitter that is configured to produce an output light that is emitting onto a surface of the flame element;
   a support member, supporting the light casing to hold the light emitter at an angle to face the flame element and to emit light onto the flame element, while allowing the light emitter to move relative to the support member;
   a drive engine coupled to the light casing and configured to cause the light casing to move on the support member and to move the light emitted from the light emitter on the flame element; and
   a movement limiting structure that limits an amount of the movement of the light casing relative to the support member in a range that prevents the emitted light from moving off the flame element,
   wherein the movement limiting structure includes a plurality of baffles, wherein each of the baffles in the plurality of baffles is positioned to interact with a tip of the support member.

* * * * *